United States Patent [19]
Whitley

[11] Patent Number: 4,686,188

[45] Date of Patent: Aug. 11, 1987

[54] PRODUCING ANAEROBIC CONDITIONS

[75] Inventor: Donald C. Whitley, Keighley, England

[73] Assignee: Don Whitley Scientific Limited, England

[21] Appl. No.: 729,372

[22] Filed: May 1, 1985

[30] Foreign Application Priority Data

May 4, 1984 [GB] United Kingdom ............... 8411531

[51] Int. Cl.⁴ ............................................. C12M 1/00
[52] U.S. Cl. .................................. 435/287; 435/313; 435/801
[58] Field of Search ...................... 435/287, 299–301, 435/29, 30, 313, 801, 809, 289

[56] References Cited

U.S. PATENT DOCUMENTS 3,775,256 11/1973 Risinger .............................. 435/801
4,111,753 9/1978 Folsom et al. ...................... 435/801

Primary Examiner—James C. Yeung
Assistant Examiner—Noah Kamen
Attorney, Agent, or Firm—William A. Drucker

[57] ABSTRACT

Anaerobic conditions are produced in a main chamber having selective communication with a lock chamber from separate supplies of anaerobe nurture gas, inert gas and oxygen-consuming gas. Flushing is from the lock chamber and oxygen-consuming gas is supplied only after flushing and first, if not only, to the lock chamber.

6 Claims, 3 Drawing Figures

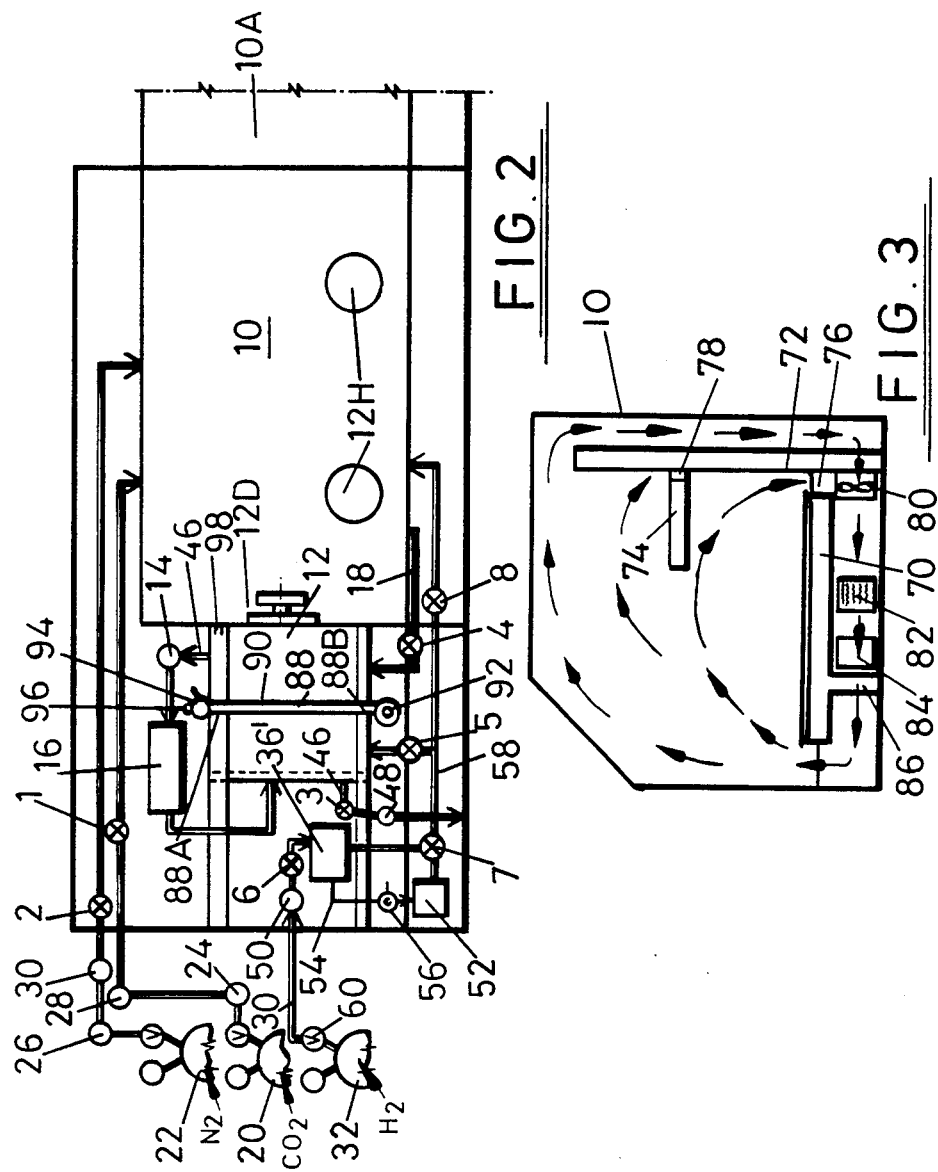

4,686,188

PRODUCING ANAEROBIC CONDITIONS

BACKGROUND OF THE INVENTION

1. Field of the Invention

The invention relates to method and apparatus for producing anaerobic conditions, typically in relation to requirements for chambers used for culturing microorganisms requiring absence of oxygen.

2. Brief Description of the Prior Art

Such requirements arise in microbiology, e.g. pathology, laboratories in the process of aiding identification of certain types of bacteria, e.g. disease-producing bacteria. Conventionally, a typical anaerobic atmosphere comprises a mixture of oxygen-consuming gas (hydrogen), an anaerobe nurture gas (carbon dioxide) and an inert gas (nitrogen), typically in ratios by volume of 1:1:8, respectively. At least in relatively advanced countries, such anaerobic gas mixture is available as such, i.e. already admixed in cylinders, but tends to be expensive compared with costs for the individual gases bought alone.

SUMMARY OF THE INVENTION

In arriving at the present invention, we addressed ourselves initially just to devising a system capable of working reliably from individual supplies of component gases of suitable anaerobic atmospheres. In doing so, however, we have developed a method, system and apparatus that has further advantages compared with prior customary practice for achieving the required atmospheres in anaerobic chambers.

Those customary practices relied basically upon repeated evacuation and flooding of the chamber, or of a lock to that chamber when loading thereto, with the anaerobic gas mixture. An acceptable procedure was to evacuate three times to 20-inch mercury gauge vacuum and to flood the chamber or lock with the anaerobic gas mixture after each evacuation. That does not eliminate all oxygen content, indeed nothing short of perfect vacuum could do so, but does reach a low enough oxygen content to be practical, at least in conjunction with some oxygen absorber for that residual content, e.g. hydrogen in the presence of a catalyst.

The method, system and apparatus of aspects of this invention utilise a different procedure that has particular advantage both from the capacity to exploit the relatively less costly availability of constituent gases alone and from reducing structural requirements by avoiding the previous requirements to withstand evacuation, i.e. very substantial reduction of internal chamber or lock pressure compared with ambient air.

Accordingly, in one specific aspect of this invention, we propose that an anaerobic chamber or lock be filled with an anaerobic atmosphere in a manner requiring or providing for flushing of that chamber or lock by a gas or gases forming part only of the final anaerobic atmosphere, conveniently in an amount corresponding to two or more, preferably three, volumes of the lock or chamber, and excluding oxygen-consuming gas.

Safety, as well as cost, is enhanced by such flushing employing only relatively inert or non-oxygen-consuming gas or gases such as the nitrogen and/or carbon dioxide components of the afore-cited mixture.

Accordingly, a preferred feature hereof is that oxygen consuming gas is added to the chamber after the aforesaid flushing.

In practice, we have found it convenient to form a first mixture of carbon dioxide and nitrogen, say at 1:9 ratio by volume, and to use that to flush the chamber or lock. In that connection, we have further found it to be entirely adequate to flush using a volume about three times that of the chamber or lock, i.e. corresponding quite closely in terms of gas-usage, to the aforesaid three-cycle evacuation/flooding practice, but not losing any relatively active oxygen-consuming gas, i.e. hydrogen in this example. After the flushing step, an injection of a given volume of hydrogen has proved to be successful generally not exceeding, actually well below 10% of the chamber or lock volume, and possibly as low as 5%. Certainly, 1 or 2 liters of injection hydrogen have proved satisfactory for a 30-liter chamber previously flushed by a flow of 90 liters of nitrogen-carbon dioxide mixture, and likely to have a maximum volume of load of about 20 liters, when 1 liter will ensure not exceeding 10% hydrogen as generally desirable in terms of safety from explosion risks.

Moreover, it is not necessary to provide the flushing gas at a considerable overpressure, in fact, it is satisfactory to operate relative to controlled gas sources and to draw the flushing gas through the lock or chamber using a pump, preferably a pump that is capable of producing some underpressure in the lock or chamber after flushing and in a manner corresponding to its relief by later addition of such further constituent gas or gases or may be desired or required, preferably from a reservoir.

In terms of the atmosphere ultimately achieved, we believe that it can be an improvement compared with the prior multiple evacuation/flooding, at least where the flushed chamber is a lock to a main chamber.

Overall, the approach hereof thus achieves all of the original objectives, including permitting lighter structures of lock and/or anaerobic chamber, and with the bonus of a better resulting atmosphere.

In addition, it will be obvious that operation relative to the lock chamber to a main anaerobic chamber further permits of effective replenishment of normally minimal hydrogen content of the main chamber via the installed lock atmosphere.

In that connection, there is provided preferred anaerobic chamber apparatus comprising a main chamber and an entry/exit lock chamber with selective communication therebetween, first means for supplying to the main chamber and thence to the lock chamber a flushing supply of part of an intended anaerobic gas atmosphere but excluding any oxygen-consuming gas, and second gas supply means for oxygen-consuming gas to the lock chamber then full of the other said part of the intended anaerobic atmosphere.

Further in that connection, there is provided a method of producing anaerobic conditions in a main chamber in selective communication with an associated entry/exit lock chamber using separate flows at prescribed relative rates of anaerobe-nuture gas, such as carbon dioxide, an inert gas, such as nitrogen, and an oxygen-consuming gas, such as hydrogen, and for which the inert gas has the greatest rate of flow, wherein such gas flow excluding oxygen consuming gas is supplied to the main chamber and thence to the lock chamber via said selective communication for flushing purposes and left to substantially fill those chambers before injecting into at least the lock chamber a prescribed volume of oxygen-consuming gas.

It is advantageous for the underpressure drawn on the lock during flushing to be exploited by pulsing of related pump means to assist disturbing gas loosely enclosed in contents of the lock chamber, e.g. air loosely trapped in petri dishes which have loose fitting covers/lids due to its atmosphere surging between pulses of pump action.

Specific implementation of this invention will now be indicated, by way of example, with reference to the accompanying drawings, in which:

BRIEF DESCRIPTION OF THE DRAWINGS

FIGS. 2 and 3 are schematic elevations and end views of a second embodiment.

DESCRIPTION OF THE PREFERRED EMBODIMENT

Figure 1:
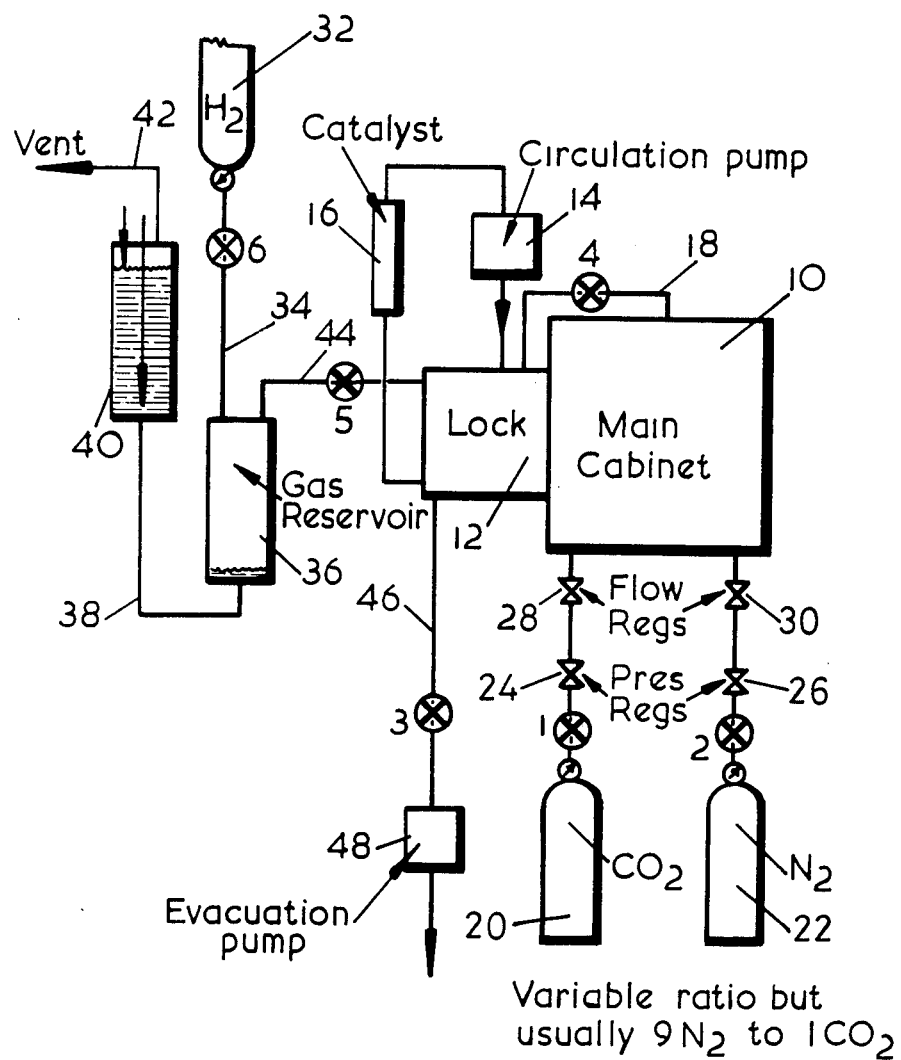
FIG. 1 is a schematic outline drawing of a first embodiment.

In FIG. 1, a main anaerobic chamber 10 has a loading lock 12, preferably with hands-on manipulation means for removing a door to the main chamber. A circulation system is shown, specifically associated with the lock 12, employing a circulation pump 14 and a catalyst stage 16, for example generally as described in our U.S. Pat. No. 2,083,497. There is also a communication 18 including a valve 4, usually of solenoid type, for servicing the atmosphere in the main chamber 10 via the lock 12 when the main chamber is otherwise closed off from the lock 12.

In connection specifically with embodying this invention, supplies for two relatively inert or nonoxygen-consuming gases, actually carbon dioxide and nitrogen, are shown at 20 and 22 as pressurised cylinders, with associated pressure regulators 24 and 26, flow regulators 28 and 30, and valves 1 and 2, also usually of solenoid type. Then, supplies of gases enable a desired ratio to be imposed, either variably or, more usually, predetermined, say 1:9 for carbon dioxide and nitrogen. These supplies are shown as being to the main chamber 10 and serve in maintaining a prescribed light overpressure, say one-inch water gauge over ambient atmosphere.

Furthermore, a source of oxygen-consuming gas is shown at 32, actually hydrogen, again as a pressurised cylinder with associated valve 6, also usually solenoid-operated, in line 34 to a gas reservoir 36 in liquid displacement connection 38 with a displacement observation or detection chamber 40 vented at 42. Another line 44 from the reservoir 36 is shown connected to the lock 12 via valve 5, and another line 46 from the lock 12 goes via valve 3 to an evacuation pump 48, the valves 3 and 5 again usually solenoid-operated.

Assuming the equipment is already set up for operation and that there is need to use the lock 12, that is done as follows. After use of the lock 12, the valves 3 and 4 are opened and the evacuation pump 48, is made to operate so that air is drawn from the lock 12, which is replaced by gas from the main chamber, which can be predominantly a mixture of the gases from the supplies 20 and 22, i.e. carbon dioxide and nitrogen in 1:9 ratio. It will be appreciated that valves 1 and 2 will also be open at this time.

When the evacuation results in a low level of oxygen in the lock 12, which could be sensed by a suitable indicator, but can conveniently be assumed after pulling through gas in an amount of about three times the volume of the lock, the valves 3 and 4 are closed. Preferably, the evacuation pump 48 can draw at least a small underpressure compared with ambient atmosphere, say about two inches water gauge, upto about two inches of mecury gauge, which will obtain when it is switched off and further assist the light overpressure in the main chamber 10 against gas flow at any time from the lock to the main chamber 10. Moreover, the evacuation pump action is preferably on a pulsed basis, whether actually so or whether only effectively so relative to the main chamber 10 by on/off control of the valve 4.

Then, operating the circulation pump 14 will circulate the gas mixture with residual oxygen in lock 12 through the catalyst stage 16. Finely divided palladium as the catalyst will be effective to induce combination of oxygen with hydrogen (forming water) and thus eliminate that residual oxygen. The hydrogen for this purpose is admitted by opening valve 5 so that hydrogen from the reservoir 26 will be drawn into the lock by the small underpressure after switching off the valve 3 and pump 48. The volume in the reservoir 36 is limited to never being able to exceed 10% of the total capacity of the lock 12 and the associated circulation system 14, 16.

That circulation operation will not usually exhaust all of the hydrogen drawn into the lock 12 from the reservoir 36, and, subsequently, the valve 5 is closed and valve 4 opened so that continued running of the circulation pump 14 will complete removal of oxygen on the lock etc.

Once catalytic removal of oxygen is complete, or sensibly taken to be complete, the main chamber door of the lock can be opened, say using gloves sealed to the lock and/or main chamber and the contents of the lock transferred to the main chamber (or vice versa) without ingress of oxygen. At the same time, any unused hydrogen will go from the lock to the main chamber and further contribute to elimination of oxygen i.e. including such that may have diffused into the main chamber 10 from the lock 12, or have otherwise resulted.

It is, of course, normally the case that the atmosphere of the main chamber is kept in virtually continous circulation through the catalyst.

The restricted volume of contents of the reservoir 36 is readily controlled by displacement on opening the valve 6 and relative to preset upper and lower levels for liquid in the chamber 40. The latter may be sensed by electrical conductivity or capacitance, a float system, or optically, with associated switching for automatic control of the valve 6 with appropriate interlock relative to operation of the other valve of the system.

It will be appreciated that the described system is highly efficient in its use of hydrogen and uses up no more than hitherto of the carbon dioxide and nitrogen. In fact, as the effective limit for hydrogen added at the lock 12 is about 10%, the main chamber 10 can never attain such levels, i.e. even at basic filling up, say by flushing through the mixture from sources 20, 22 and completion of de-oxygenating via the lock 12 and hydrogen.

The embodiment of FIGS. 2 and 3 is generally similar to that of FIG. 1 but shown in more detail and with some differences in its features and operation. The same references are used where appropriate.

Concerning handling of hydrogen, purging of the lock 12 is alternatively achieved by using a reservoir 36' at a regulated pressure of about 12 psi, see regulator 50, and a timer 52 for controlling exit from the reservoir 36' shown via valve 7, as a predetermined pulse of hydrogen. There is an interlock 54 between the reservoir 36' and the timer 52, including a pressure gauge switch 56 to ensure that the reservoir 36' is up to pressure before each operation of the timer 52 for opening the valve 7. The valve 6 is, of course, still desirable as a basic hydrogen control relative to the reservoir 36', also the valve 5 for routing to the lock 12 from output 58 of the valve 7. In addition, for safety reasons, it is further preferred that valve 60 from the hydrogen cylinder 32 is of an automatic pressure-sensitive shut-off type, say so operating at 25 psi.

In addition, line 58 from the hydrogen pulse valve 7 is shown going to the main chamber 10 via another valve 8, and is intended for use at least in first charging of the main chamber 10 and lock 12, typically as two further hydrogen pulses after the pulse to the lock 12. That can, of course, be part of standard procedure at lock purging as the amount of gas removed via the lock is three times its volume and each hydrogen pluse is no more than a tenth of that volume, i.e. the overall hydrogen content of the system cannot increase. Such procedure will undoubtedly be preferred for at least some installations. Then, if not otherwise, it is preferred that communication from the main chamber 10 to the lock 12 for forced circulation purposes be of small aperture and thus high resistance, actually requiring a larger evacuation pump 48 than the lock-only circulation pump 14, say drawing an underpressure of 2 inches mercury gauge. FIG. 2 further indicates a preferred capability to attach at least one additional main working chamber, see 10A. Also, ports 12H are indicated for hands-on glove units to the main chamber, and sealing door 12D from the main chamber 10 to the lock 12.

Turning to FIG. 3, a preferred main chamber 10 is shown with a floor 70 spaced above its bottom, a wall 72 spaced from its back, and a shelf 74 extending from the wall 72. Connection between the wall 72 and the floor 70, shelf 74, see 76, 78 respectively, allows gas passage therethrough, i.e. past rear edges of the floor 70 and shelf 74. Provision is made for circulation as indicated by the arrows driven by a fan 80, through heaters 82 and over catalyst at 84, then between floor supports 86 all below the floor 70.

The lock is shown with a sliding door 88 in top and bottom guides 88A, 88B with a pivotal securement handle 90 on a lower pivot 92 spring-loaded to its open or down position (not shown) and having an upper fixing clamp 94. There are also microswitches 96 and 98 associated with the clamp 94 and the door 88 as interlocks to ensure that flushing/purging operations cannot begin until the door 88 is properly closed.

I claim:

1. A method of producing anaerobic conditions comprising the steps of:
    (a) providing a main chamber in selective communication with an associated entry/exit lock chamber,
    (b) providing separate flows at prescribed relative rates of anaerobe-nurture gas, an inert gas, and an oxygen-consuming gas, and for which the inert gas has the greatest rate of flow,
    (c) supplying such gas flow excluding oxygen-consuming gas to the main chamber and thence to the lock chamber via said selective communication for flushing and filling said chambers therewith,
    (d) injecting into at least the lock chamber a prescribed volume of oxygen consuming gas; and then
    (e) further including providing a catalyst in communication with at least said lock chamber and subjecting the contents of the lock chamber which includes said oxygen-consuming gas to said catalyst for oxygen-consuming action.

2. A method according to claim 1, further including opening said selective communication and then drawing the flushing flow of gas from the lock chamber before the injection of oxygen-consuming gas.

3. A method according to claim 2, further including restricting flow through said selective communication so that drawing gas from the lock chamber produces a lower pressure in the latter than in the main chamber, and the drawing of gas from the main chamber is done on a pulsed basis.

4. A method according to claim 1, where said anaerobe-nuture gas, inert gas and oxygen-consuming gas comprise carbon dioxide, nitrogen, and hydrogen respectively.

5. A method according to claim 2, where said anaerobe-nuture gas, inert gas, and oxygen-consuming gas comprise carbon dioxide, nitrogen, and hydrogen respectively.

6. A method according to claim 3, where said anaerobe-nuture gas, inert gas and oxygen-consuming gas comprise carbon dioxide, nitrogen, and hydrogen respectively.

* * * * *